United States Patent
Weissheimer et al.

(10) Patent No.: US 9,981,889 B2
(45) Date of Patent: May 29, 2018

(54) USE OF DIETHYLENETRIAMINE AS A CS2 SCAVENGER IN ISOPRENE PRODUCTION

(71) Applicant: GENERAL ELECTRIC COMPANY, Schenectady, NY (US)

(72) Inventors: Flavio Weissheimer, Cotia (BR); John Link, Humble, TX (US)

(73) Assignee: General Electric Company, Schenectady, NY (US)

( * ) Notice: Subject to any disclaimer, the term of this patent is extended or adjusted under 35 U.S.C. 154(b) by 0 days. days.

(21) Appl. No.: 14/913,500

(22) PCT Filed: Aug. 15, 2014

(86) PCT No.: PCT/US2014/051241
§ 371 (c)(1),
(2) Date: Feb. 22, 2016

(87) PCT Pub. No.: WO2015/026649
PCT Pub. Date: Feb. 26, 2015

(65) Prior Publication Data
US 2016/0207854 A1   Jul. 21, 2016

Related U.S. Application Data

(60) Provisional application No. 61/868,634, filed on Aug. 22, 2013.

(51) Int. Cl.
*C07C 11/18* (2006.01)
*C07C 7/148* (2006.01)
(Continued)

(52) U.S. Cl.
CPC ........ *C07C 7/14875* (2013.01); *B01D 53/485* (2013.01); *B01D 53/8606* (2013.01);
(Continued)

(58) Field of Classification Search
CPC ................................ C07C 7/148; C07C 11/18
(Continued)

(56) References Cited

U.S. PATENT DOCUMENTS 2,982,796 A   5/1961   Veal
3,012,947 A   12/1961  Kelley et al.
(Continued)

FOREIGN PATENT DOCUMENTS

CN   1057663 A    1/1992
CN   102423623 A  4/2012
(Continued)

OTHER PUBLICATIONS

Wang et al., "Homogeneous Catalyzed Reaction of Carbon Disulfide and O-Phenylene Diamine by Tetrabutylamminium Hydroxide in the Presence of Potassium Hydroxide", Chinese Institute of Chemical Engineers, vol. No. 38, Issue No. 01, pp. 85-90, Jun. 6, 2007.
(Continued)

*Primary Examiner* — Ellen M McAvoy
(74) *Attorney, Agent, or Firm* — Wegman, Hessler & Vanderburg

(57) ABSTRACT

Methods for scavenging carbon disulfide ("$CS_2$") from hydrocarbon streams using treatment compositions comprising at least one $CS_2$ scavenger and at least one phase transfer catalyst therein. The $CS_2$ scavenger may comprise at least one polyamine with the general formula: $H_2N-(R_1-NH)_x-R_2-(NH-R_3)_y-NH_2$ wherein $R_1$, $R_2$, $R_3$ may be the same or different H, aryl or $C_1$-$C_4$ alkyl; and x and y may be integers from 0 to 10. A hydrocarbon product with a reduced concentration of $CS_2$ therein.

14 Claims, 1 Drawing Sheet

(51) Int. Cl.
*B01D 53/48* (2006.01)
*B01D 53/86* (2006.01)

(52) U.S. Cl.
CPC ...... *C07C 11/18* (2013.01); *B01D 2252/2053* (2013.01); *B01D 2252/20415* (2013.01); *B01D 2252/20421* (2013.01); *B01D 2252/20426* (2013.01); *B01D 2252/602* (2013.01); *B01D 2255/70* (2013.01); *B01D 2256/24* (2013.01)

(58) Field of Classification Search
USPC ............. 508/545, 558, 547; 208/208 R, 236
See application file for complete search history.

(56) References Cited

U.S. PATENT DOCUMENTS

| | | |
|---|---|---|
| 3,692,861 A | 9/1972 | Chikatsu et al. |
| 3,775,259 A | 11/1973 | Sarno |
| 3,860,496 A | 1/1975 | Ginnasi et al. |
| 4,147,848 A | 4/1979 | Arakawa et al. |
| 4,401,838 A | 8/1983 | Balogh |
| 5,104,557 A | 4/1992 | Lindstrom |
| 6,858,686 B2 | 2/2005 | Laubry |
| 7,427,385 B2* | 9/2008 | Scheirer ................. B01D 53/75 423/244.01 |
| 7,566,687 B2* | 7/2009 | Zaid ....................... C10G 29/20 208/208 R |
| 8,597,501 B2* | 12/2013 | Krupa ..................... C10G 21/08 208/177 |
| 9,441,169 B2* | 9/2016 | Gargano ................. C10G 27/04 |
| 9,670,596 B2* | 6/2017 | Koide ....................... D01F 2/02 |
| 2003/0205134 A1 | 11/2003 | Hasenberg et al. |
| 2008/0161576 A1 | 7/2008 | Guggenheim et al. |
| 2012/0232319 A1 | 9/2012 | Gartside et al. |
| 2014/0088334 A1* | 3/2014 | Krupa ..................... C10G 19/08 585/833 |

FOREIGN PATENT DOCUMENTS

| | | |
|---|---|---|
| GB | 617969 A | 2/1949 |
| JP | 2005281602 A * | 10/2005 |
| WO | 2009120419 A1 | 10/2009 |

OTHER PUBLICATIONS

Unofficial English Translation of Chinese Office Action issued in connection with corresponding CN Application No. 201480046463.X dated Oct. 17, 2016.

International Search Report and Written Opinion dated Oct. 31, 2014 which was issued in connection with PCT Patent Application No. PCT/US14/051241 which was filed on Aug. 15, 2014.

* cited by examiner

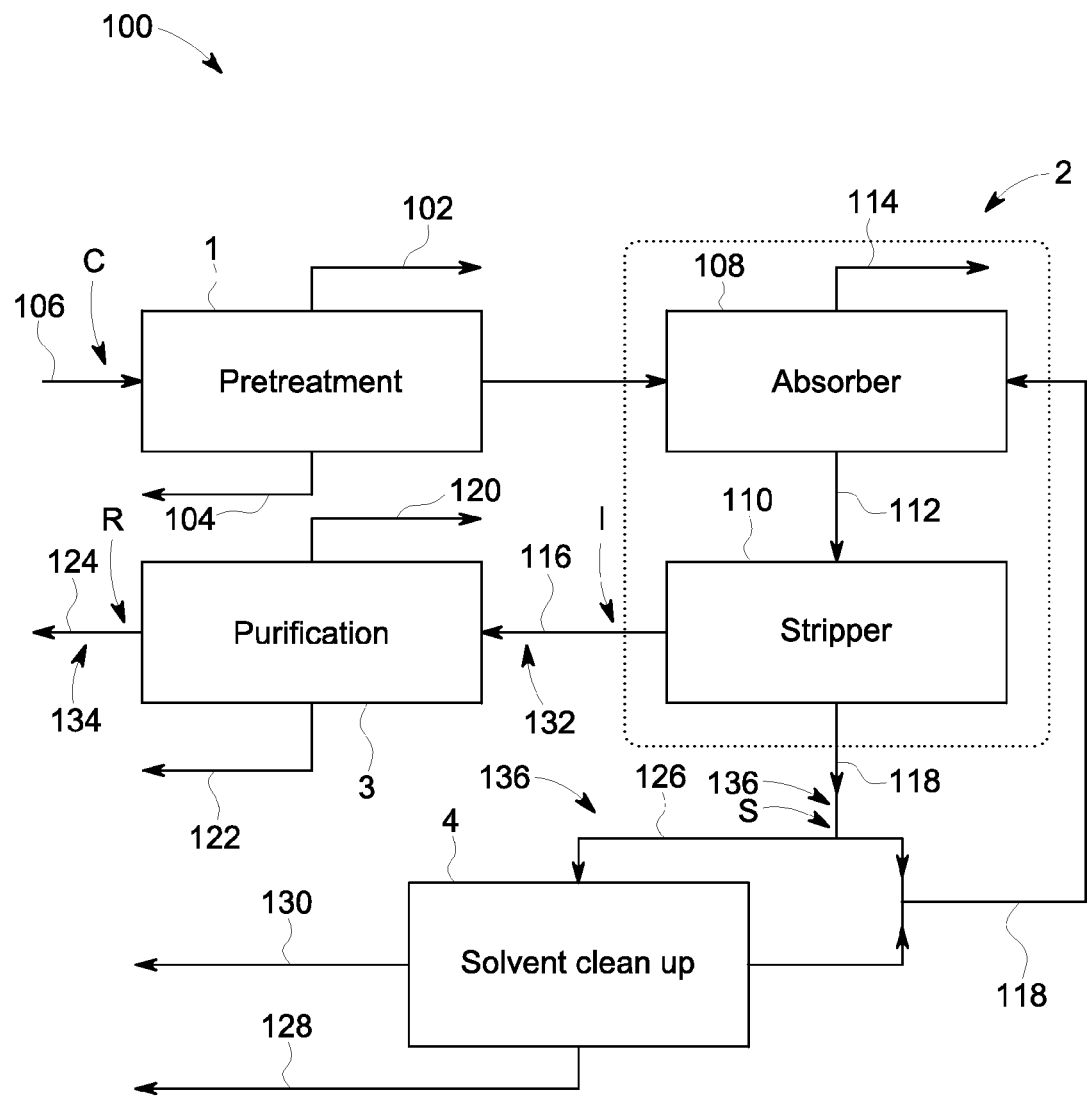

USE OF DIETHYLENETRIAMINE AS A CS2 SCAVENGER IN ISOPRENE PRODUCTION

CROSS REFERENCE TO RELATED APPLICATION

This application is a national stage application under 35 U.S.C. § 371(c) of prior filed, co-pending PCT application serial number PCT/US2014/051241, filed on Aug. 15, 2014, which claims priority to U.S. Provisional Patent Application Ser. No. 61/868,634 filed Aug. 22, 2013, titled USE OF DIETHYLENETRIAMINE AS A $CS_2$ SCAVENGER IN ISOPRENE PRODUCTION. The above-listed applications are herein incorporated by reference.

FIELD OF THE INVENTION

This disclosure relates to scavenging carbon disulfide ($CS_2$) from hydrocarbon streams.

BACKGROUND OF THE INVENTION

Isoprene is polymerized in the production of synthetic rubber. The physical properties of synthetic rubber are highly dependent on the underlying microstructure. Polymer chains of mixed microstructure results in synthetic rubber of lower quality than synthetic rubbers of a single microstructure repeated in an orderly fashion. Synthetic rubber producers prefer high-purity isoprene since it produces a synthetic rubber with a highly uniform microstructure and with desirable physical properties.

Carbon disulfide, ("$CS_2$") is often present in $C_5$ naphtha used to make isoprene. $CS_2$ may poison catalysts used to facilitate removal of other hydrocarbon impurities in the isoprene or Ziegler catalysts used in the polymerization process. Unfortunately, $CS_2$ and isoprene have similar boiling points, thus it is difficult to remove $CS_2$ through distillation. Thus, scavengers comprising polyamines are frequently used in isoprene production to react with the $CS_2$ and facilitate its removal from the isoprene.

BRIEF DESCRIPTION OF THE INVENTION

Carbon disulfide scavenging efficiencies from hydrocarbon streams may be increased by adding a phase transfer catalyst. Accordingly, methods for scavenging $CS_2$ from hydrocarbons using a treatment composition comprising a phase transfer catalyst are disclosed. The method may comprise contacting the hydrocarbon stream with a treatment composition to form a reaction product of $CS_2$ and the treatment composition. The treatment composition may comprise at least one $CS_2$ scavenger and at least one phase transfer catalyst therein. The $CS_2$ scavenger may comprise at least one polyamine with the general formula:

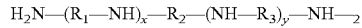

wherein $R_1$, $R_2$, $R_3$ may be the same or different H, aryl or $C_1$-$C_4$ alkyl; and x and y may be integers from 0 to 10. The reaction product may then be separated from the hydrocarbon stream. In another method, the polyamine may be diethylenetriamine ("DETA").

The phase transfer catalyst may comprise at least one quaternary ammonium salt with the general formula:

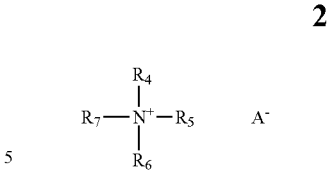

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion.

In another method, at least one quaternary ammonium salt may be selected from the group consisting of alkyl quaternary ammonium salts, dialkyl fatty ammonium salts, dimethyl dialkyl ammonium salts, and diamide ammonium complexes. In yet another embodiment, at least one quaternary ammonium salt may be selected from the group consisting of tetradecyldimethylbenzylammonium chloride (zephiramine) and tetrabutylammonium bromide ("TBAB").

In another method, the hydrocarbon stream may comprise isoprene. In another method, the hydrocarbon stream may comprise a solvent stream in an isoprene purification process. In yet embodiment, the solvent stream may be a lean solvent stream that is contacted with the treatment composition as the lean solvent stream exits a stripper in the isoprene purification process.

In another embodiment, the ratio of the amount of $CS_2$ scavenger to the amount of $CS_2$ may range from about 1 to about 5 moles of $CS_2$ scavenger per mole of $CS_2$.

In another embodiment, a treatment composition for scavenging carbon disulfide in a hydrocarbon stream is disclosed. The treatment composition may comprise at least one $CS_2$ scavenger and at least one phase transfer catalyst therein. The $CS_2$ scavenger may comprise at least one polyamine with the general formula:

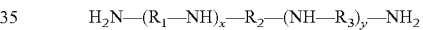

wherein $R_1$, $R_2$, $R_3$ may be the same or different H, aryl or $C_1$-$C_4$ alkyl; and x and y may be integers from 0 to 10. In another embodiment, the polyamine may be diethylenetriamine.

In another embodiment, the weight of the phase transfer catalyst is 0.1 to 10% of the $CS_2$ scavenger. In another embodiment, the treatment composition may have a phase transfer catalyst comprising at least one quaternary ammonium salt with the general formula:

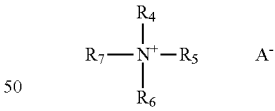

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion.

The phase transfer catalyst may comprise at least one quaternary ammonium salt selected from the group consisting of alkyl quaternary ammonium salts, dialkyl fatty ammonium salts, dimethyl dialkyl ammonium salts, and diamide ammonium complexes. In yet another embodiment, at least quaternary ammonium salt may be selected from the group consisting of tetradecyldimethylbenzylammonium chloride (zephiramine) and tetrabutylammonium bromide.

In another embodiment, a hydrocarbon product with a reduced concentration of carbon disulfide therein is disclosed. The $CS_2$ may be reduced in a method comprising contacting the hydrocarbon product with a treatment composition to form a reaction product of the $CS_2$ and the treatment composition. The treatment composition may comprise at least one $CS_2$ scavenger and at least one phase transfer catalyst therein. The $CS_2$ scavenger may comprise at least one polyamine with the general formula:

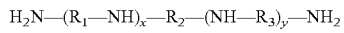

$$H_2N—(R_1—NH)_x—R_2—(NH—R_3)_y—NH_2$$

wherein $R_1$, $R_2$, $R_3$ may be the same or different H, aryl or $C_1$-$C_4$ alkyl; and x and y may be integers from 0 to 10. The reaction product may then be separated from the hydrocarbon product. In another embodiment, the polyamine may be diethylenetriamine.

The phase transfer catalyst may comprise at least one quaternary ammonium salt with the general formula:

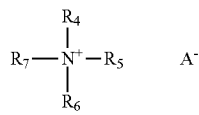

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion.

In another embodiment, the phase transfer catalyst may comprise at least one quaternary ammonium salt selected from the group consisting of alkyl quaternary ammonium salts, dialkyl fatty ammonium salts, dimethyl dialkyl ammonium salts, and diamide ammonium complexes. In another embodiment, at least one quaternary ammonium salt may be selected from the group consisting of tetradecyldimethylbenzylammonium chloride (zephiramine) and tetrabutylammonium bromide. In yet another embodiment, the hydrocarbon product may comprise isoprene.

BRIEF DESCRIPTION OF THE DRAWINGS

FIG. 1 shows a simplified isoprene production process.

DETAILED DESCRIPTION

FIG. 1 shows a portion of a simplified process 100 wherein isoprene is produced by extraction (or purified) from a crude $C_5$ stream that was produced from the steam cracking of naphtha. Variations to the simplified process depicted may occur without limiting the scope of the invention. The process may be divided into four general sections:

1. A pretreatment section 1 where light ends ($\leq C_4$ components) 102 and heavy ends ($\geq C_6$ components) 104 are removed from the crude $C_5$ feed 106. This section typically consists of dimer drums that convert cyclopentadiene to dicyclopentadiene ("DCPD"). DCPD and piperylene are also removed in the pretreatment section.

2. An extractive distillation section 2 is comprised of an absorber 108 and a stripper 110. In the absorber 108, isoprene is absorbed in a suitable aprotic solvent (typically acetonitrile or dimethylformamide) 112 and sent to the stripper 110. Pentanes and pentenes are not absorbed in the solvent and are removed in the absorber overhead as raffinate 114. The isoprene rich solvent is stripped and the $C_5$ components 116 are sent to the purification section 3. The stripped solvent (lean solvent) 118 is recirculated to the absorber 108.

3. In the purification section 3, $C_5$ acetylenes 120, and water and heavy components (collectively 122) are removed yielding pure isoprene 124.

4. A slipstream 126 of the lean solvent 118 from the stripper bottoms is sent to a solvent clean up section 4 where heavy components 128 and light components 130 are removed from the solvent, such as by distillation. The components present in streams 128 and 130 can include antifoam, polymer, water and solvent degradation products. Antifoam and polymers are typically present in the heavy component stream 128 and water and solvent degradation products may be present in one or both streams 128 and 130. The source of water into the overall process can be the $C_5$ feed 106 or the solvent used in the absorber 108.

A treatment composition may be added to stream 106 going into the pretreatment section 1, the stream going into the absorber, stream 112 going into the stripper, stream 116 going into the purification section 3, stream 118 going into the solvent clean up section 4 or going into the absorber 108, stream 126 going into the solvent clean up section 4, and stream 124 leaving the purification section 3, or a combination in various locations. For example, the treatment composition may be added to the isoprene stream before it enters the purification section 3 as shown at 132. In another example, the treatment composition may also be added to the finished isoprene at 134 after the purification section 3 or to the lean solvent 118 at 136 leaving the stripper 110 or before entering the solvent clean up section 4. The treatment composition reacts with the $CS_2$ present in the isoprene stream or the lean solvent to form water-soluble reaction products such as dithiocarbamate salts, which will be primarily absorbed by water in the isoprene streams or water in the solvent streams. Once the water is removed, the water-soluble reaction products are removed with the water. If the treatment composition is added to the finished isoprene at 134, a wash step may be necessary to remove the water with the reactant products since the purification section 3 will have removed much of the water present.

In one embodiment, the treatment composition may be added to the lean solvent 118 as it leaves the stripper 110. The formed dithiocarbamate salts may be removed in the solvent clean up section 4 with the heavy components 128. The ultimate goal is to remove the $CS_2$ from the isoprene stream, and removing $CS_2$ from the solvent allows the solvent to better remove the $CS_2$ from the isoprene.

In some embodiments, the treatment composition may be added to the lean solvent 118 as it leaves the stripper 110 and before it enters a solvent clean up section comprising two distillation towers (not shown). The first tower distills solvent and water overhead, leaving polymer, antifoam, any remaining treatment composition, and the dithiocarbamate salts to be removed as heavies. The second tower receives the first tower overhead in addition to water from a water wash column (not shown). These combined streams will remove the acetonitrile/water azeotrope (constant boiling mixture) overhead while excess water goes to the bottoms in the second tower and is reused as the water feed for the water wash column.

Carbon disulfide scavenging efficiencies from hydrocarbon streams may be increased by adding a phase transfer catalyst. Accordingly, methods for scavenging $CS_2$ from hydrocarbons using a treatment composition comprising a phase transfer catalyst are disclosed. The method may comprise contacting the hydrocarbon stream with a treatment composition to form a reaction product of $CS_2$ and the treatment composition. The treatment composition may comprise at least one $CS_2$ scavenger and at least one phase transfer catalyst therein. The CS₂ scavenger may comprise at least one polyamine with the general formula:

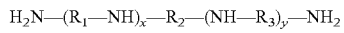

wherein R₁, R₂, R₃ may be the same or different H, aryl or C₁-C₄ alkyl; and x and y may be integers from 0 to 10. In another method, the polyamine may be diethylenetriamine.

The reaction product may then be separated from the hydrocarbon stream. The reaction product and the hydrocarbon stream may be separated using any method anticipated by those of ordinary skill in the art. Suitable methods include, but are not limited to, washing and distillation.

The phase transfer catalyst may comprise at least one quaternary ammonium salt with the general formula:

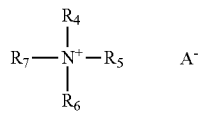

wherein n is a positive whole number; R₄, R₅, R₆, and R₇ may be the same or different H, aryl, benzyl, or C₁-C₂₀ alkyl, and A⁻ may be a hydroxide, halide, acetate, sulfate, or nitrate anion.

In another method, at least one quaternary ammonium salt may be selected from the group consisting of alkyl quaternary ammonium salts, dialkyl fatty ammonium salts, dimethyl dialkyl ammonium salts, and diamide ammonium complexes. In yet another embodiment, at least one quaternary ammonium salt may be selected from the group consisting of tetradecyldimethylbenzylammonium chloride (zephiramine) and tetrabutylammonium bromide.

The amount of treatment composition required to reduce the amount of carbon disulfide from the hydrocarbon stream may vary depending on a variety of factors, including the amount of CS₂ present. In one embodiment the treatment composition may be present in a range of about 0.1 ppm to about 10,000 ppm by volume of the hydrocarbon stream. In another embodiment, the treatment composition may be present in a range of about 1 ppm to about 5000 ppm. In yet another embodiment, the treatment composition may range from about 1 ppm to about 1000 ppm. In another method, the hydrocarbon stream may comprise isoprene. In yet another method, the hydrocarbon stream may be contacted with the treatment composition as the hydrocarbon stream enters an isoprene wash vessel, which is not shown in FIG. 1 but can be added as part of the isoprene production or purification process.

The reaction products may include dithiocarbamate salts.

In another embodiment, a treatment composition for scavenging carbon disulfide in a hydrocarbon stream is disclosed. The treatment composition may comprise at least one CS₂ scavenger and at least one phase transfer catalyst therein. The CS₂ scavenger may comprise at least one polyamine with the general formula:

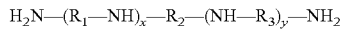

wherein R₁, R₂, R₃ may be the same or different H, aryl or C₁-C₄ alkyl; and x and y may be integers from 0 to 10. In yet another embodiment, the polyamine may be diethylenetriamine.

In another embodiment, the phase transfer catalyst is 0.1 to 10% of the weight of the CS₂ scavenger. Alternatively, the phase transfer catalyst may range from about 1 to 5% of the weight of the CS₂ scavenger.

In another embodiment, the treatment composition may have a phase transfer catalyst comprising at least one quaternary ammonium salt with the general formula:

wherein R₄, R₅, R₆, and R₇ may be the same or different H, aryl, benzyl, or C₁-C₂₀ alkyl, and A⁻ may be a hydroxide, halide, acetate, sulfate, or nitrate anion.

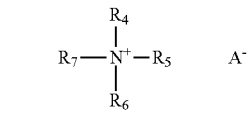

The phase transfer catalyst may comprise at least one quaternary ammonium salt selected from the group consisting of alkyl quaternary ammonium salts, dialkyl fatty ammonium salts, dimethyl dialkyl ammonium salts, and diamide ammonium complexes. In yet another embodiment, the at least one quaternary ammonium salt may be selected from the group consisting of tetradecyldimethylbenzylammonium chloride (zephiramine) and tetrabutylammonium bromide.

In another embodiment, a hydrocarbon product with a reduced concentration of carbon disulfide therein is disclosed. The CS₂ may be reduced using a method comprising contacting the hydrocarbon product with a treatment composition to form a reaction product of the CS₂ and the treatment composition. The treatment composition may comprise at least one CS₂ scavenger and at least one phase transfer catalyst therein. The CS₂ scavenger may comprise at least one polyamine with the general formula:

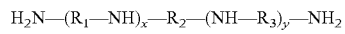

wherein R₁, R₂, R₃ may be the same or different H, aryl or C₁-C₄ alkyl; and x and y may be integers from 0 to 10. The reaction product may then be separated from the hydrocarbon product.

In another embodiment, the polyamine may be diethylenetriamine. The phase transfer catalyst may comprise at least one quaternary ammonium salt with the general formula:

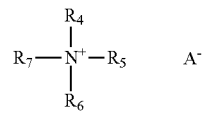

wherein R₄, R₅, R₆, and R₇ may be the same or different H, aryl, benzyl, or C₁-C₂₀ alkyl, and A⁻ may be a hydroxide, chloride, acetate, sulfate, or nitrate anion.

In another embodiment, the phase transfer catalyst may comprise at least one quaternary ammonium salt selected from the group consisting of alkyl quaternary ammonium salts, dialkyl fatty ammonium salts, dimethyl dialkyl ammonium salts, and diamide ammonium complexes. In another embodiment, at least one quaternary ammonium salt may be selected from the group consisting of tetradecyldimethylbenzylammonium chloride (zephiramine) and tetrabutylammonium bromide.

In another method, the hydrocarbon stream may comprise isoprene. In another method, the hydrocarbon stream may comprise a solvent stream in an isoprene purification process. In yet embodiment, the solvent stream may be a lean solvent stream that is contacted with the treatment composition as the lean solvent stream exits a stripper in the isoprene purification process.

EXAMPLES

Although DETA is a known $CS_2$ scavenger, prior to embodiments of the present invention, it was thought that tetraethylene pentamine ("TEPA") was far superior to DETA in removing $CS_2$. TEPA is typically added to the pretreatment section 1 to react with the $CS_2$ and form a dithiocarbamate salt. When TEPA is used, the dithiocarbamate salt produced is a strong chelate that promotes corrosion downstream of the pretreatment unit. DETA however, produces a dithiocarbamate salt that is an active chelate and less corrosive than the TEPA salt. Despite TEPA's impact on corrosion, however, some isoprene producers found its superior scavenging properties made it more particular to DETA. U.S. Pat. No. 4,401,838 ('838 patent) discloses the use of several compounds to remove $CS_2$. At column 5, the '838 patent discloses that tetraethylene pentamine (TEPA), on an equimolar basis, is 10 times as effective as the next compound on a list, which is diethylene triamine (DETA). Even if this calculation is adjusted to be on a mass basis instead of a molar basis (due to the different molar masses of TEPA and DETA), TEPA would still be more than five times better than DETA since the molecular weight of DETA is more than half that of TEPA. Thus, conventional knowledge, as demonstrated by the '838 patent, is that TEPA is far superior to DETA in the removal of $CS_2$. However, as shown in the examples below, embodiments of the present invention surprisingly is able to use a catalyst to make DETA significantly better than TEPA to remove $CS_2$.

Isoprene producers sometimes measure the amount of $CS_2$ that goes into a system, as well as the amount of that $CS_2$ which is present in the resulting isoprene, since the $CS_2$ is undesirable in the isoprene. The performance of a particular $CS_2$ scavenger may also be monitored by calculating a performance index, denoted as PI. The performance index is based on the following formula PI=(SR/CI)*1000. S is the amount of scavenger added to the lean solvent in kg/hour. R is the amount of residual $CS_2$ in the finished isoprene 124 (in parts per million) after the purification section 3. C is the amount of $CS_2$ going into the system from the crude $C_5$s 106 in parts per million. I is the amount of isoprene 116 going into the purification section 3. The resultant number is multiplied by 1000 for convenience to avoid an index which is less than one.

Since the numerator contains the amount of scavenger added and the residual $CS_2$ and the denominator has the amount of $CS_2$ going into the system and the amount of isoprene treated, a high PI shows a less effective product. This is because when the PI is high, it means that for each unit of $CS_2$ going into the system and/or each unit of isoprene processed, it requires more scavenger and/or results in more residual $CS_2$. Thus, it is desirable to have a lower PI rather than a higher PI.

Comparative Example 1

Runs were conducted in which isoprene was produced and purified, and TEPA was added to remove $CS_2$ from the system. Specifically, the amount of $CS_2$, C, that was present in the crude $C_5$s 106 was measured in ppm. TEPA was added (S, in kg/hr) to the lean solvent 118 coming out of the stripper 110 to remove $CS_2$ from the lean solvent stripped from the isoprene. With this method, minimal, if any, scavenger is carried over into the isoprene. The amount of isoprene, I, going into the purification section 3 was also measured in kg/hr. The amount of $CS_2$, R, in the finished isoprene 124 was also measured after the purification section 3. Since not all of the $CS_2$ present in the crude $C_5$s ends up in the isoprene and due to variability in the system, dozens of data points over a number of days were taken for reliability purposes and an average PI was calculated from the data. The result was an average PI of 5.79.

Example 1

For Example 1, the same methodology was used as in Comparative Example 1, except that instead of using TEPA, DETA was used in combination with 1.61% of N-Benzyl-N,N-dimethyl-1-dodecanaminium chloride relative to the DETA. Dozens of data points were obtained and resulted in an average PI of 2.35.

Since PI is inversely related to the performance in removal of $CS_2$, Example 1 showed a significant improvement over Comparative Example 1. In Example 1, the PI is 59.4% less than the PI of Comparative Example 1, and therefore, it is significantly better. This is surprising in view of the fact that, prior to embodiments of the present invention, TEPA was known to be superior to DETA in removing $CS_2$.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

The invention claimed is:

1. A method of scavenging carbon disulfide ("$CS_2$") in a hydrocarbon stream comprising:
   (a) contacting said hydrocarbon stream with a treatment composition to form a reaction product of said $CS_2$ and said treatment composition, wherein said hydrocarbon stream comprises isoprene, wherein said treatment composition comprises at least one $CS_2$ scavenger and at least one phase transfer catalyst therein and wherein said $CS_2$ scavenger comprises at least one polyamine with the general formula:

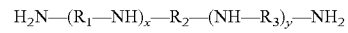

wherein $R_1$, $R_2$, $R_3$ may be the same or different H, aryl or $C_1$-$C_4$ alkyl; and x and y are integers from 0 to 10; and
   (b) separating the reaction product from said hydrocarbon stream,
      wherein said phase transfer catalyst comprises at least one quaternary ammonium salt with the general formula:

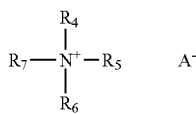

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion, and wherein at least one quaternary ammonium salt is selected from the group consisting of alkyl quaternary ammonium salts, dialkyl fatty ammonium salts, dimethyl dialkyl ammonium salts, and diamide ammonium complexes.

2. The method of claim 1, wherein said polyamine is diethylenetriamine ("DETA").

3. The method of claim 1, wherein at least one quaternary ammonium salt is selected from the group consisting of tetradecyldimethylbenzylammonium chloride (zephiramine) and tetrabutylammonium bromide ("TBAB").

4. The method of claim 1, wherein said hydrocarbon stream comprises a solvent stream in an isoprene purification process.

5. The method of claim 4, wherein said solvent stream is a lean solvent stream that is contacted with said treatment composition as said lean solvent stream exits a stripper in said isoprene purification process.

6. A treatment composition for scavenging carbon disulfide ("$CS_2$") in a hydrocarbon stream, wherein said hydrocarbon stream comprises isoprene, said treatment composition comprising at least one $CS_2$ scavenger and at least one phase transfer catalyst therein and wherein said $CS_2$ scavenger comprises at least one polyamine with the general formula:

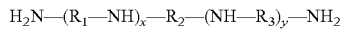

wherein $R_1$, $R_2$, $R_3$ may be the same or different H, aryl or $C_1$-$C_4$ alkyl; and x and y are integers from 0 to 10.

7. The treatment composition of claim 6, wherein a weight of the phase transfer catalyst is 0.1 to 10% of a weight of the $CS_2$ scavenger.

8. The treatment composition of claim 6, wherein said polyamine is diethylenetriamine ("DETA").

9. The treatment composition of claim 6, wherein said phase transfer catalyst comprises at least one quaternary ammonium salt with the general formula:

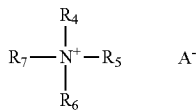

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion.

10. The treatment composition of claim 9, wherein at least one quaternary ammonium salt is selected from the group consisting of alkyl quaternary ammonium salts, dialkyl fatty ammonium salts, dimethyl dialkyl ammonium salts, and diamide ammonium complexes.

11. The treatment composition of claim 9, wherein at least one quaternary ammonium salt is selected from the group consisting of tetradecyldimethylbenzylammonium chloride (zephiramine) and tetrabutylammonium bromide ("TBAB").

12. A hydrocarbon product with a reduced concentration of carbon disulfide ("$CS_2$") therein, wherein said $CS_2$ was reduced in a method comprising:

(a) contacting said hydrocarbon product with a treatment composition to form a reaction product of said $CS_2$ and said treatment composition, wherein said hydrocarbon product comprises isoprene, wherein said treatment composition comprises at least one $CS_2$ scavenger and at least one phase transfer catalyst therein and wherein said $CS_2$ scavenger comprises at least one polyamine with the general formula:

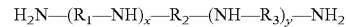

wherein $R_1$, $R_2$, $R_3$ may be the same or different H, aryl or $C_1$-$C_4$ alkyl; and x and y are integers from 0 to 10; and (b) separating the reaction product from said hydrocarbon product, wherein said phase transfer catalyst comprises at least one quaternary ammonium salt with the general formula:

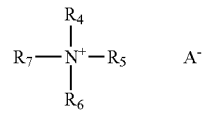

wherein $R_4$, $R_5$, $R_6$, and $R_7$ may be the same or different H, aryl, benzyl, or $C_1$-$C_{20}$ alkyl, and $A^-$ may be a hydroxide, halide, acetate, sulfate, or nitrate anion, and wherein at least one quaternary ammonium salt is selected from the group consisting of alkyl quaternary ammonium salts, dialkyl fatty ammonium salts, dimethyl dialkyl ammonium salts, and diamide ammonium complexes.

13. The hydrocarbon product of claim 12, wherein said polyamine is diethylenetriamine ("DETA").

14. The hydrocarbon product of claim 12, wherein at least one quaternary ammonium salt is selected from the group consisting of tetradecyldimethylbenzylammonium chloride (zephiramine) and tetrabutylammonium bromide ("TBAB").

* * * * *